(12) United States Patent
Tockman et al.

(10) Patent No.: US 7,280,876 B1
(45) Date of Patent: Oct. 9, 2007

(54) LEAD DELIVERY SYSTEM HAVING FEATURES TO FACILITATE TORQUING

(75) Inventors: Bruce A. Tockman, Scandia, MN (US); John S. Greenland, San Diego, CA (US); Gary L. Hauge, Carlsbad, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 192 days.

(21) Appl. No.: 10/992,359

(22) Filed: Nov. 18, 2004

(51) Int. Cl.
*A61N 1/05* (2006.01)
(52) U.S. Cl. ..................................... 607/125
(58) Field of Classification Search ......... 607/115–125
See application file for complete search history.

(56) References Cited

U.S. PATENT DOCUMENTS

| | | | |
|---|---|---|---|
| 5,423,772 A | 6/1995 | Lurie et al. | |
| 5,549,581 A | 8/1996 | Lurie et al. | |
| 5,643,231 A | 7/1997 | Lurie et al. | |
| 5,722,963 A | 3/1998 | Lurie et al. | |
| 5,728,143 A | 3/1998 | Gough et al. | |
| 5,846,229 A | 12/1998 | Berg | |
| 5,984,909 A | 11/1999 | Lurie et al. | |
| 6,001,085 A | 12/1999 | Lurie et al. | |
| 6,027,460 A | 2/2000 | Shturman | |
| 6,132,417 A | 10/2000 | Kiesz | |
| 6,277,107 B1 | 8/2001 | Lurie et al. | |
| 6,301,507 B1 | 10/2001 | Bakels et al. | |
| 6,321,123 B1 | 11/2001 | Morris et al. | |
| 6,458,107 B1 | 10/2002 | Ockuly | |
| 6,611,710 B2 | 8/2003 | Gomperz et al. | |
| 6,656,166 B2 | 12/2003 | Lurie et al. | |
| 6,758,854 B1 | 7/2004 | Butler et al. | |
| 2004/0006329 A1 | 1/2004 | Scheu | |
| 2004/0019359 A1* | 1/2004 | Worley et al. | ............... 606/129 |

* cited by examiner

*Primary Examiner*—Scott M. Getzow
(74) *Attorney, Agent, or Firm*—Faegre & Benson LLP

(57) ABSTRACT

The present invention is a medical assembly comprising an elongated flexible medical device, such as a cardiac lead, and a torquing member, such as a stylet, slidably receivable inside the medical device. The device and member are coupled at their distal ends by a corresponding set of opposing curves. This coupling allows more precise rotational control of the assembly when it is manipulated at its proximal end. In one embodiment, the assembly has a open curvature at its distal end. In another embodiment, the distal end has a closed curvature.

22 Claims, 4 Drawing Sheets

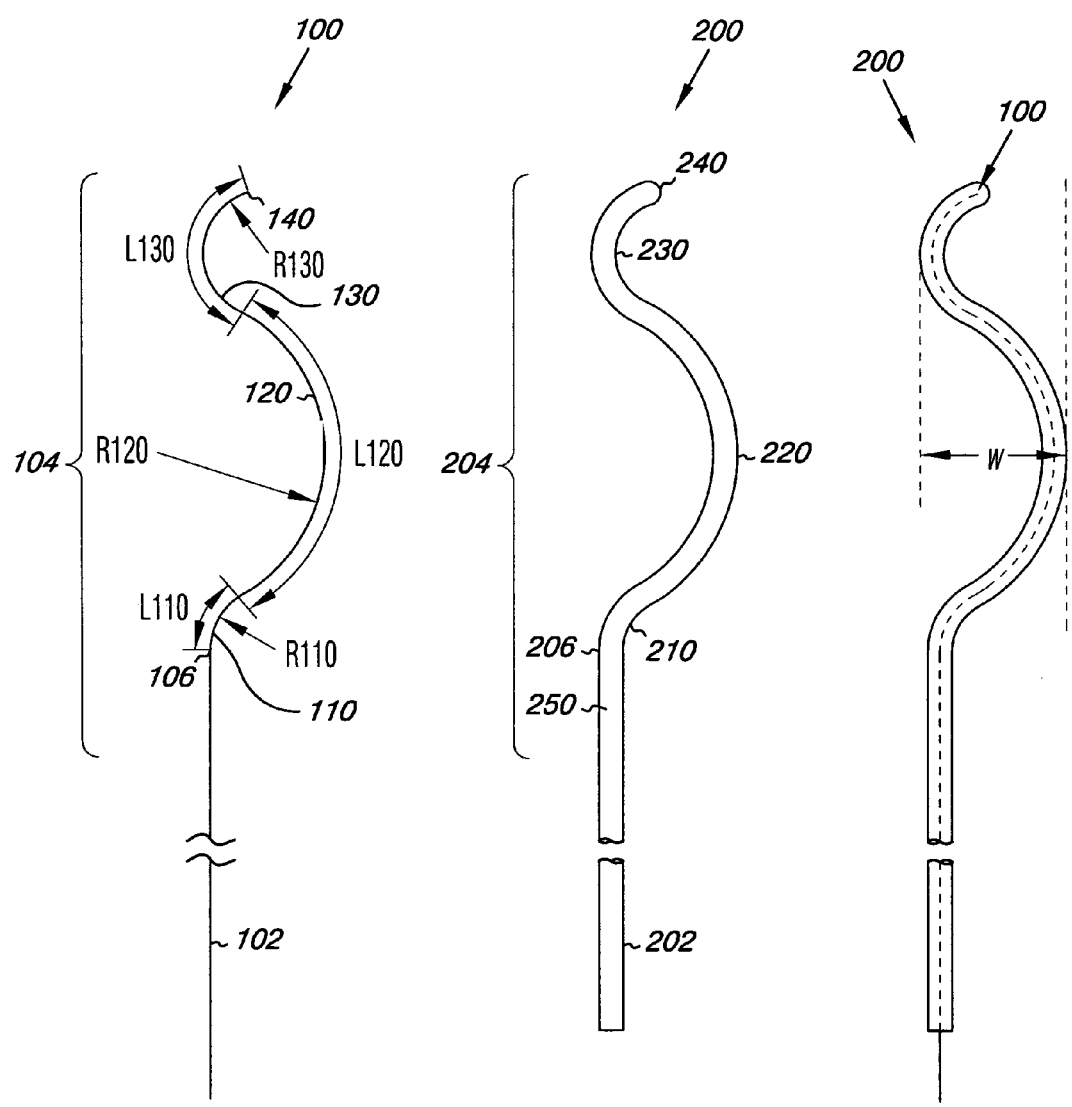
*Fig. 2A*  *Fig. 2B*  *Fig. 2C*

LEAD DELIVERY SYSTEM HAVING FEATURES TO FACILITATE TORQUING

TECHNICAL FIELD

The present invention relates to a lead having improved rotational steerability at a distal end. The present invention further relates to the use of stylets and/or guide wires in combination with a lead for providing improved rotational steerability at the distal end of the lead.

BACKGROUND

Implantable medical devices for treating irregular contractions of the heart with electrical stimuli are well known in the art. Some of the most common forms of such implantable devices are defibrillators and pacemakers. Various types of electrical leads for defibrillators and pacemakers have been suggested in the prior art.

A broad group of leads may be characterized by the fact that they are placed transvenously. These leads are introduced into the patient's vasculature at a venous access site and travel through veins to the locations where the leads' electrodes will implant in or otherwise contact coronary tissue. One large subfamily of the group of transvenously-placed leads are those that are implanted in the endocardium (the tissue lining the inside of the heart) of the right atrium or ventricle. Another subfamily that is becoming increasingly used are those leads that are placed in the branch vessels of the coronary venous system.

In general, directing a lead through a patient's vasculature can be a challenging proposition for a cardiac physician. For example, those leads that are placed in a branch vessel of the coronary venous system must be navigated to the right atrium of the heart, into the coronary sinus through the coronary sinus ostium, and then into a desired branch vessel. To assist in such lead placements, a physician will typically use a device such as a guide wire or catheter with a pre-formed bend at its distal end. By rotationally manipulating the proximal end of the device, the distal end of the device can be pointed in a preferred direction, for example, toward a branch entrance. After the device has been placed, a lead will then follow either over the guide wire or within the catheter to the site.

On occasion, a physician might wish to deploy a lead without first navigating another device in advance to the electrode placement site. The flexible nature of leads, though, is such that they exhibit very little "steerability" or distal response to proximal manipulation. One response to this problem is to deploy a lead with a stylet or guide wire (hereafter simply referred to as a stylet) residing in the lead's central lumen to provide shape and steerability to the lead. The stylet would then be removed when lead placement was achieved. Stylets, however, can rotate within the lead lumen. Thus rotation of the stylet does not always impart rotation to the lead. This limits the ability of the physician to rotationally steer the distal end of the lead via proximal manipulation of the stylet.

There is a need in the art for a way of providing torque to the distal end of an implantable lead. There is a further need for providing torque to the distal end of an implantable lead with a stylet.

SUMMARY

The present invention is a rotatable medical assembly for navigating a human vasculature. In one embodiment, the assembly comprises an elongated flexible medical device including a lumen extending along its length. The medical device has a proximal portion and a distal portion. The assembly also comprises a torquing member receivable in the lumen and extending substantially from the proximal to distal portions of the medical device. The torquing member has a member proximal portion and a member distal portion. The member distal portion includes a first curve and a second curve having opposing curvatures. When the torquing member is positioned in the lumen, the torquing member forms corresponding curves in the distal portion of the medical device, such that a torque applied to the member proximal portion is transferred to the distal portion of the medical device.

In another embodiment, the invention is a left-ventricular cardiac pacing device comprising a lead having an elongated, flexible body including a lumen extending along its length, the lead having a proximal portion and a distal portion; and a torquing means for effecting rotation of the distal portion of the lead.

In yet another embodiment, the present invention is a method of advancing a lead into a patient's coronary venous system. The method comprises embedding a distal end of a guiding catheter in the patient's coronary sinus ostium. A lead having an elongated, flexible body including a lumen extending along its length, the lead having a proximal portion and a distal portion, is provided. A stylet receivable in the lumen and extending substantially from the proximal to the distal portions of the lead is provided. The stylet has a stylet proximal portion and a stylet distal portion. The stylet distal portion includes a first curve and a second curve having opposing curvatures. When the stylet is positioned in the lumen, forming a lead assembly, the stylet forms corresponding curves in the lead distal portion, such that a torque applied to the stylet proximal portion is transferred to the distal portion of the lead; and advancing the lead assembly through the guiding catheter into the patient's coronary sinus.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2A is a plan view of a stylet with compound shapes ending in a generally open distal curve.

FIG. 2B is a plan view of a lead having a shape substantially similar to that of the stylet of FIG. 2A.

FIG. 2C is a plan view of the stylet of FIG. 2A and lead of FIG. 2B slidably connected with compound shapes registered.

Figure 1:
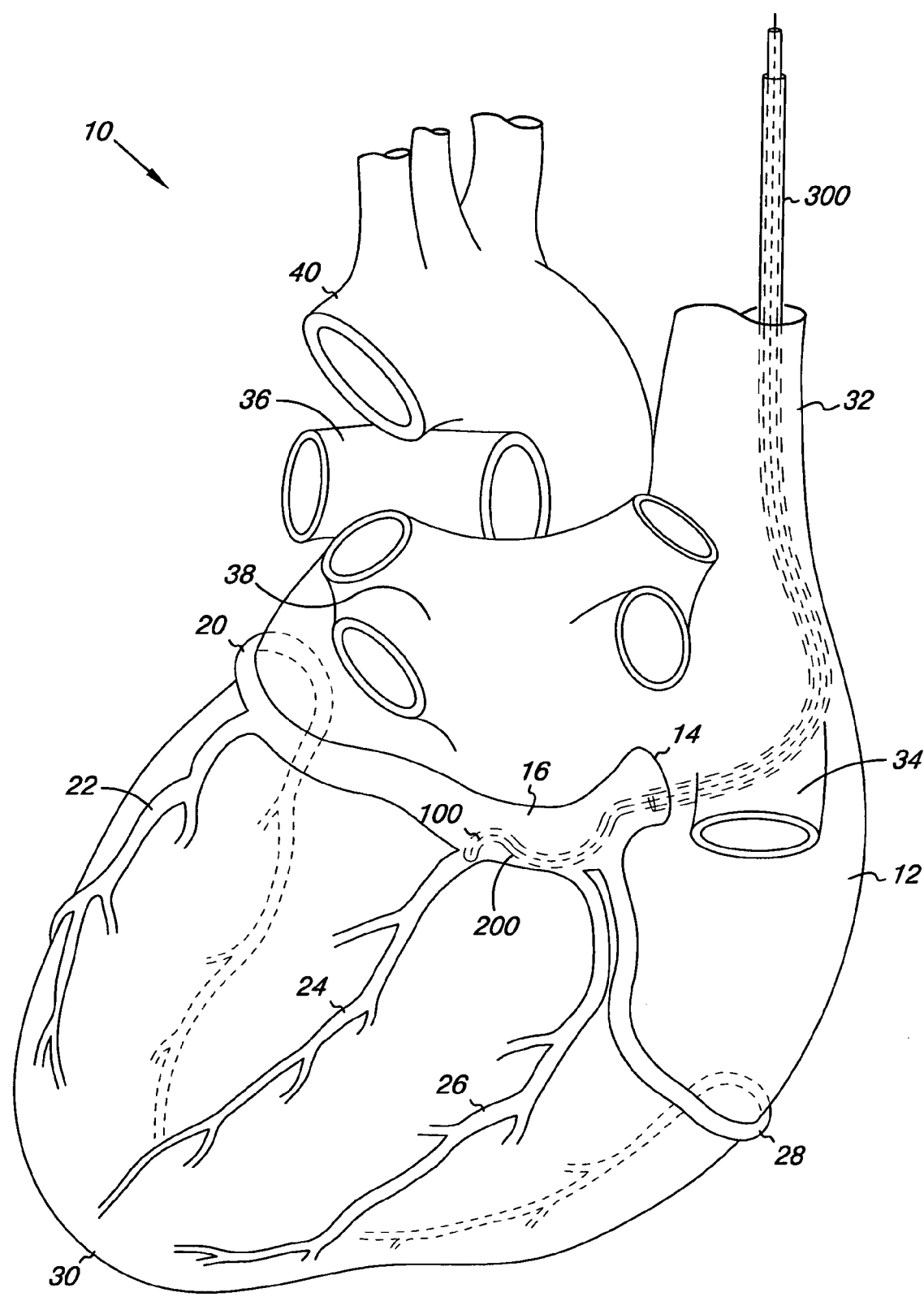
FIG. 1 is a left-posterior perspective view of a human heart showing a stylet and lead during implantation according to the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The present invention, in one embodiment, is directed to lead delivery components used to facilitate implantation of leads in the coronary veins. In other embodiments, the invention may be used for lead delivery to other parts of the anatomy, including for example the right atrium and ventricle of the heart. FIG. 1 is a left-posterior perspective view of a human heart 10 showing a stylet 100, a lead 200, and a guiding catheter 300 during an implantation process. FIG. 1 also illustrates the major coronary veins. The majority of coronary blood flow returns to the right atrium 12 via the coronary sinus ostium 14. The coronary sinus ostium 14 provides access to the coronary sinus 16, which extends laterally across the posterior surface of the heart 10, through the coronary groove, from the ostium 14 to the great cardiac vein 20. The coronary sinus 16 typically has a length of from about 2 to about 10 cm and a width of from about 4 to about 14 mm. The great cardiac vein 20 extends around the heart 10 and along its anterior surface. Near the junction with the great cardiac vein 20, the coronary sinus 16 connects with the left marginal vein 22. Near its midpoint, the coronary sinus 16 connects with the left posterior ventricular vein 24. Near the ostium 14, the coronary sinus 16 connects with the middle cardiac vein 26 and the small cardiac vein 28. Note that the great cardiac vein 20, left marginal vein 22, left posterior ventricular vein 24, middle cardiac vein 26, and small cardiac vein 28 all lead downward toward the apex 30 of the heart.

FIG. 1 also shows the major vessels entering and leaving the heart 10. The superior vena cava 32 and inferior vena cava 34 return blood to the right atrium 12 from the extremities of the circulatory system. The pulmonary arteries 36 direct blood from the right ventricle to the lungs and the pulmonary veins 38 return oxygenated blood from the lungs to the left atrium. Finally the aorta 40 directs blood flow exiting the left ventricle.

FIG. 2A is a plan view showing a torquing member, such as a guide wire or a stylet 100, according to one embodiment of the present invention. The stylet has a proximal portion 102 and a distal portion 104. While the proximal portion 102 is generally straight, the distal portion 104 is pre-formed with an advantageous compound shape beginning at deflection location 106. The compound shape comprises three co-planar parts: a proximal curve 110, a middle curve 120, and a distal curve 130. In other embodiments, the compound shape may not lie solely in one plane. The distal curve 130 is generally open, or J-shaped. The stylet 100 terminates in a distal tip 140.

FIG. 2B is a sectional view showing medical device, such as a lead 200, having a shape substantially similar to that of the stylet 100 of FIG. 2A. The lead 200 has a proximal portion 202 and a distal portion 204. The proximal portion 202 is generally straight and the distal portion 204 is pre-formed with an advantageous compound shape beginning at deflection location 206. The compound shape comprises three co-planar parts: a proximal curve 210, a middle curve 220, and a distal curve 230. The distal curve 230 is generally open, or J-shaped. The lead 200 terminates in a distal tip 240 and is hollow, having a central lumen 250.

The compound shape of the distal portion 104 of the stylet 100 is formed by techniques known in the art. The lead is generally flexible to allow cannulation of the vasculature. A variety of techniques known in the art may be used to form the compound shape 204 of the lead. The lead 200 includes a conductor coil surrounded by a polymer body. In one embodiment, the compound shape 204 is heat set into the polymer body during manufacture. In another embodiment, the shape is formed during the conductor coiling process. In yet other embodiments, "tendons" or other additional shaping parts are embedded in the polymer body during manufacture.

The compound shapes of the distal portions 104 and 204 of both the stylet 100 and lead 200 of FIGS. 2A and 2B are substantially identical. In one exemplary embodiment, the proximal curves 110 and 210 have radii R110 of about 5 mm and arc lengths L110 of about 5 mm, the middle curves 120 and 220 have radii R120 of about 10 mm (curving in a sense opposite to that of the proximal curves) and arc lengths L120 of about 21 mm, and the distal curves 130 and 230 have radii R130 of about 4 mm (curving in a sense opposite to that of the middle curves) and arc lengths L130 of about 9 mm.

In other embodiments, the proximal curves 110 and 210 have radii R110 of from about 3 to about 7 mm and arc lengths L110 of from about 3 to about 7 mm, the middle curves 120 and 220 have radii R120 of from about 6 to about 14 mm (curving in a sense opposite to that of the proximal curves) and arc lengths L120 of from about 13 to about 29 mm, and the distal curves 130 and 230 have radii R130 of from about 3 to about 5 mm (curving in a sense opposite to that of the middle curves) and arc lengths L130 of about 7 to about 11 mm.

The stylet 100 is slidably receivable within the lumen 250 of the lead 200. When the stylet 100 is fully seated within the lead 200, as shown in FIG. 2C, the corresponding curves of the distal portions 104 and 204 of each unit are registered with each other. The assembled stylet 100 and lead 200 will be referred to hereinafter as "the lead assembly 100/200." The compound shape comprising curves 110/210, 120/220, and 130/230 of the lead assembly 100/200 has an overall width dimension, w, sized to fit within the coronary sinus. In the exemplary embodiment described above, the width w is about 9 mm. In other embodiments, the width w is from about 4 to about 14 mm. In yet other embodiments, the width, w, is from about 7 to about 11 mm.

In the lead assembly 100/200, the registration of the compound shapes of the stylet 100 and lead 200 serves to couple their respective distal portions 104 and 204. As a consequence of this coupling, a rotation of the proximal portion 102 of the stylet causes the distal portion 104/204 of the lead assembly 100/200 to rotate as well. Without the coupling, the stylet 100 would be free to rotate independently of the lead 200. The present invention, therefore, enables the stylet 100 to act as a torquing member that provides improved control over the rotational displacement of the distal portion 104/204 of the lead assembly 100/200 through manipulation of its proximal portion 102. In some embodiments, the proximal portions 102 and 202 of the stylet 100 and lead 200 are reversibly coupled or locked to prevent relative motion and enhance rotational control.

Figures 3A, 3B, 3C:
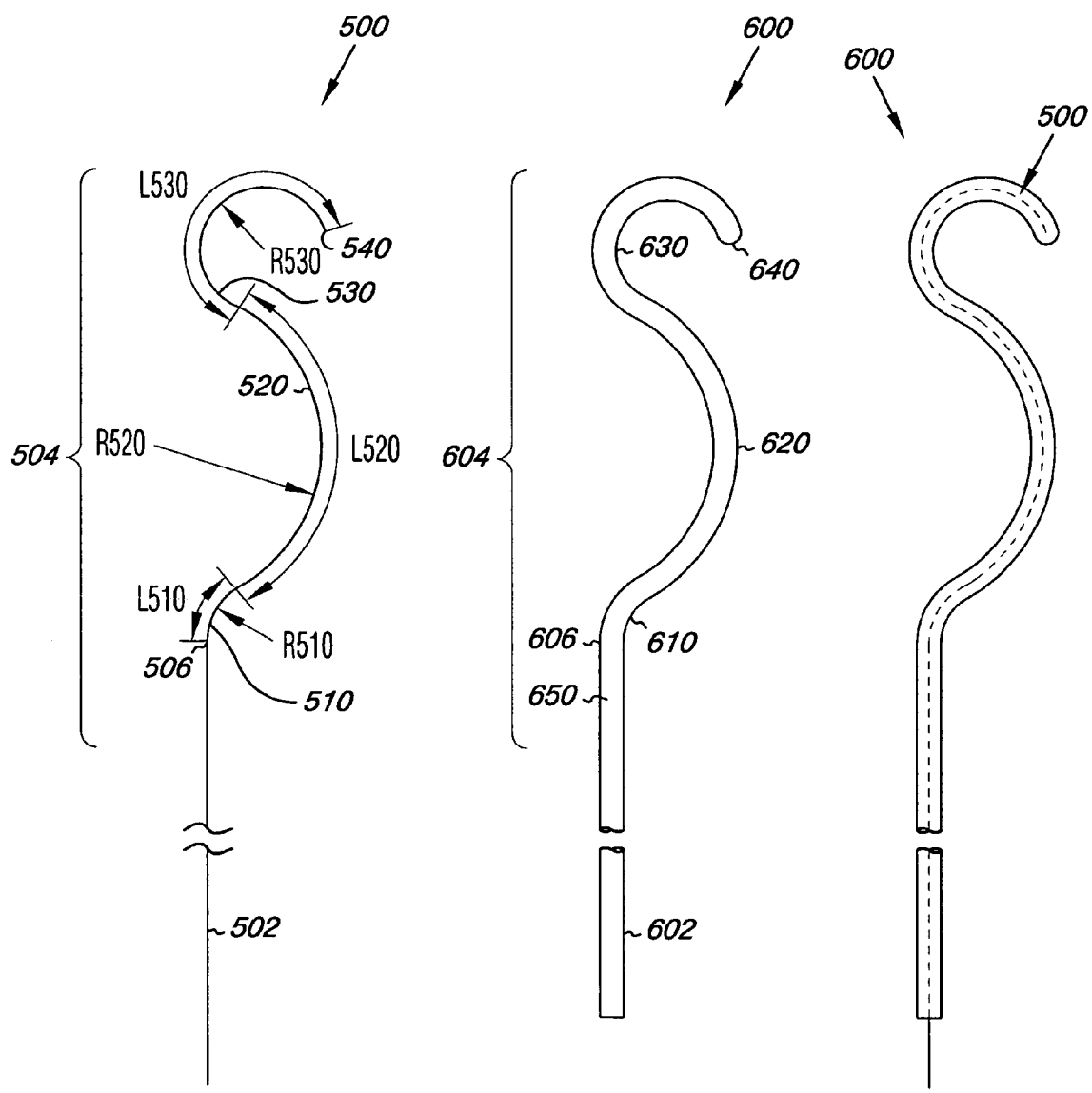
FIG. 3A is a plan view of a stylet with compound shapes ending in a generally closed distal curve.
FIG. 3B is a plan view of a lead having a shape substantially similar to that of the stylet of FIG. 3A.
FIG. 3C is a plan view of the stylet of FIG. 3A and lead of FIG. 3B slidably connected with compound shapes registered.

FIG. 3A is a plan view showing a stylet 500 according to another embodiment of the present invention. The stylet has a proximal portion 502 and a distal portion 504. The proximal portion 502 is generally straight and the distal portion 504 is pre-formed with an advantageous compound shape beginning at deflection location 506. The compound shape comprises three co-planar parts: a proximal curve 510, a middle curve 520, and a distal curve 530. The distal curve 530 is generally closed, or hook-shaped. The stylet 500 terminates in a distal tip 540.

FIG. 3B is a sectional view showing a lead 600 having a shape substantially similar to that of the stylet 500 of FIG. 3A. The lead 600 has a proximal portion 602 and a distal portion 604. The proximal portion 602 is generally straight and the distal portion 604 is pre-formed with an advantageous compound shape beginning at deflection location 606. The compound shape comprises three co-planar parts: a proximal curve 610, a middle curve 620, and a distal curve 630. The distal curve 630 is generally closed, or hook-shaped. The lead 600 terminates in a distal tip 640 and is hollow, having a central lumen 650.

The compound shapes of the distal portions 504 and 604 of both the stylet 500 and lead 600 of FIGS. 3A and 3B are substantially identical. In one embodiment, the proximal curves 510 and 610 have radii R510 of about 5 mm and arc lengths L510 of about 5 mm, the middle curves 520 and 620 have radii R520 of about 10 mm (curving in a sense opposite to that of the proximal curves) and arc lengths L520 of about 21 mm, and the distal curves 530 and 630 have radii R530 of about 4 mm (curving in a sense opposite to that of the middle curves) and arc lengths L530 of about 15 mm.

In other embodiments, the proximal curves 510 and 610 have radii R510 of from about 3 to about 7 mm and arc lengths L510 of from about 3 to about 7 mm, the middle curves 520 and 620 have radii R520 of from about 6 to about 14 mm (curving in a sense opposite to that of the proximal curves) and arc lengths L520 of from about 13 to about 29 mm, and the distal curves 530 and 630 have radii R530 of from about 3 to about 5 mm (curving in a sense opposite to that of the middle curves) and arc lengths L530 of about 11 to about 19 mm.

In the same manner as that described for the embodiment depicted in FIGS. 2A, B, and C, the stylet 500 and lead 600 of the embodiment depicted in FIGS. 3A and 3B fit together slidably as depicted in FIG. 3C to form a rotationally coupled lead assembly 500/600.

Yet other embodiments include a stylet-lead assembly having only two curved segments. For example, the stylet 500 may not include the distal curve 530, so long as the opposing proximal curve 510 and the middle curve 520 are sufficient to rotationally couple the stylet 500 and the lead 600. In still other embodiments, the compound shape is not restricted to a single plane. Some shapes may include sub-shapes lying in multiple planes. In other embodiments, the distal shape may curve continuously through three-dimensional space. A helix is one example of such a shape. In general, an infinite variety of shapes can achieve the function of coupling a stylet and lead in a lead assembly, and the dimensions of the curves may, in general, vary with the application. Different vasculature navigation goals may suggest certain shapes and methods. Specific torquing requirements may be best achieved with particular shapes. Furthermore, individual physicians may prefer using certain shapes.

In another embodiment, the lead 200 or 600 does not include pre-formed curved segments. In this embodiment, the curvature of the stylet imparts a generally corresponding curvature to the lead to accomplish the desired rotational coupling. In yet another embodiment, the medical device is a catheter having diagnostic or therapeutic functions.

Figure 4:
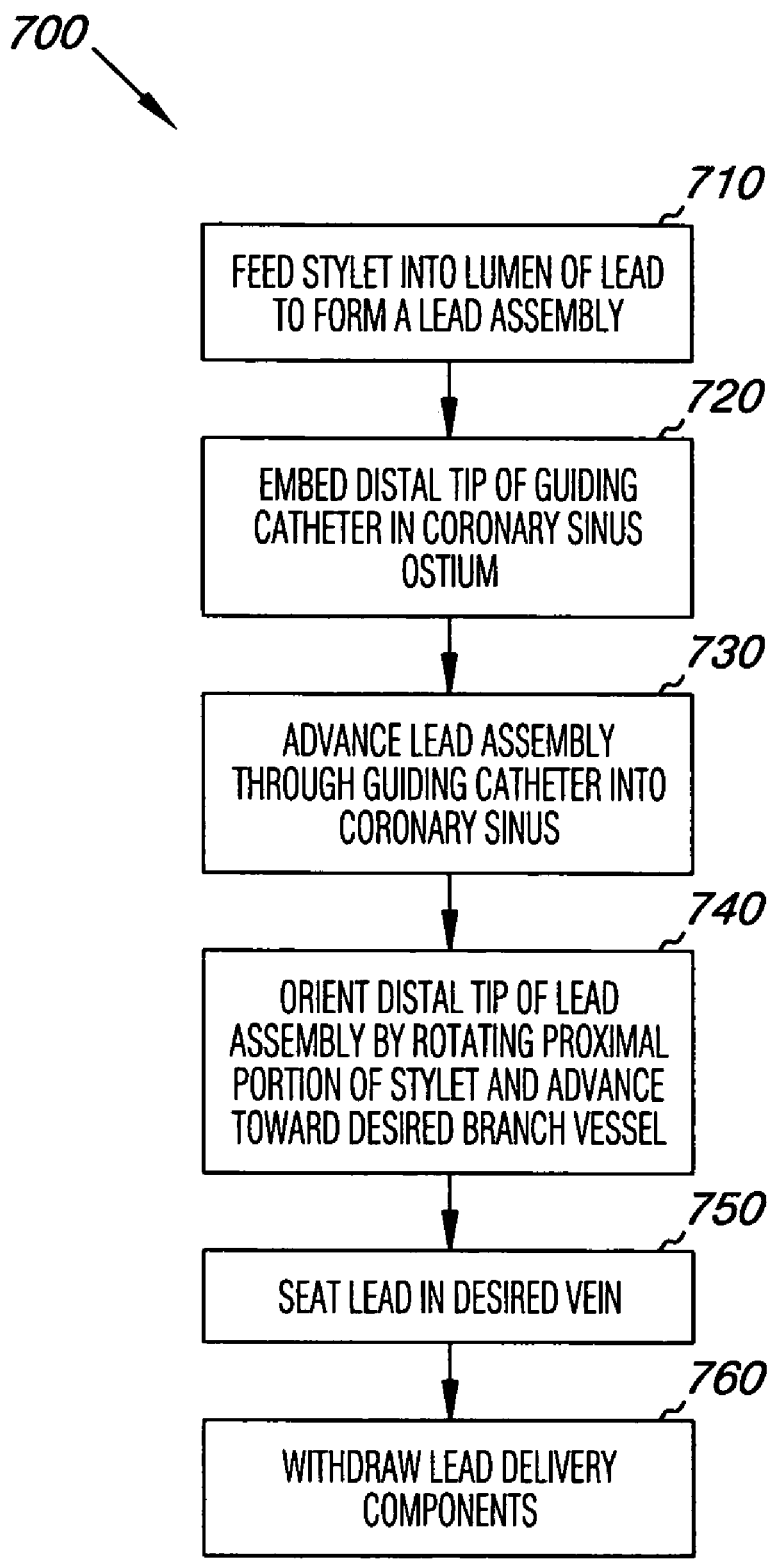
FIG. 4 is a flowchart describing a method of placing a lead in the coronary venous system according to an embodiment of the present invention.

The flowchart of FIG. 4 shows a method 700, according to one embodiment of the present invention, for placing the lead 200 in a branch vessel, such as the left marginal vein 22, where it can supply electrical stimulation to the heart 10 at a suitable location for accomplishing rhythm management (e.g., close to its apex 30). In the following description, it may be helpful to refer to FIG. 1, which illustrates an intermediate point in the method 700.

Before use, the lead assembly 100/200 is formed by sliding the stylet 100 into the lumen 250 of the lead 200 until it is fully seated and the corresponding curves of the distal portions 104 and 204 are registered (block 710). A commonly known surgical technique is used to advance a guiding catheter 300 from a venous access site to the coronary sinus ostium 14 (block 720). Once the guiding catheter 300 is in place, the lead assembly 100/200 is advanced into the catheter (block 730). The assembly 100/200 is sufficiently flexible so that it will readily conform approximately to the shape of the guiding catheter 300 and slide freely within it. In particular, the pre-formed compound shape of the distal portion 104/204 of the lead assembly 100/200 is straightened by the guiding catheter 300. Once the distal portion 104/204 emerges from the guiding catheter 300 into the coronary sinus 16, it returns elastically to its pre-formed shape, as shown in FIG. 1. Note that the shape of the distal portion 104/204 is designed to fit substantially without distortion in the coronary sinus 16.

Once the lead assembly 100/200 is located in the coronary sinus 16, the physician uses conventional imaging techniques to assess the suitability of its orientation for advancement into the desired branch vessel for chronic placement of the lead 200. By rotating the assembly 100/200, the off-centered distal tip 140/240 can be pointed toward an opening of a branch vessel that the physician wishes to access, or it may be rotated away from an opening so that the assembly will continue further into the coronary sinus 16 as it is advanced. It is during such a rotation of the lead assembly 100, 200 that the present invention enables improved rotational control of the distal portion 104/204 and distal tip 140/240 via manipulation of the proximal portion of the stylet 102 by the physician. In the process of deploying the lead assembly 100/200 to the desired branch vessel, the physician may alternate between rotating and advancing the assembly multiple times (block 740).

After the physician advances the lead assembly 100/200 into the desired branch vessel, the lead is seated by a method known in the art (block 750). The stylet 100 is then withdrawn, along with the guiding catheter 300 and any other lead delivery components (block 760).

In another embodiment, the present invention is used to adjust the position of a lead electrode within a vessel once it has reached a desired implantation site. Leads are commonly placed in coronary veins on the surface of the heart (e.g., as described in method 100). One side of the vein is adjacent to heart muscle, and the other side faces outward into the pericardial space. It may be desirable to rotationally orient the lead such that the electrode is closer to the muscle side, where better performance may be achieved. In addition, there may be disadvantages to having the electrode on the outer side of the vein. For example, the vein may be close to or in contact with one of the phrenic nerves, which control the diaphragm. Unintended stimulation of a phrenic nerve can result in an undesired hiccup-like response. Careful orientation of a lead within a vein can greatly reduce this possibility.

Various modifications and additions can be made to the exemplary embodiments discussed without departing from the scope of the present invention. Although the detailed description has described the use of stylets and leads, other torquing members and elongated, flexible medical devices may benefit from the present invention as well. Accordingly, the scope of the present invention is intended to embrace all such alternatives, modifications, and variations as fall within the scope of the claims, together with all equivalents thereof.

We claim:

1. A rotatable medical apparatus for navigating a human vasculature, the apparatus comprising:
   an elongated flexible lead including a lumen extending along its length, the lead having a proximal portion and a distal portion, a pre-formed lead first curve and a pre-formed lead second curve having opposing curvatures; and
   a torquing member receivable in the lumen and extending substantially from the proximal to distal portions of the lead, the torquing member having a member proximal portion and a member distal portion, the member distal portion including a first curve and a second curve substantially similar to the curves of the lead;
   wherein when the torquing member is positioned in the lumen, a torque applied to the member proximal portion is transferred to the distal portion of the lead.

2. The apparatus of claim 1 wherein the torquing member is selected from the group consisting of: a guide wire and a stylet.

3. The apparatus of claim 1 wherein the member distal portion terminates in an open or J-shape.

4. The apparatus of claim 1 wherein the member distal portion terminates in a closed or hook-shape.

5. The apparatus of claim 1 wherein the torquing member distal portion further includes a third curve having a curvature opposing the curvature of the second curve.

6. The apparatus of claim 5 wherein the first, second, and third curves are co-planar, and further wherein the first curve has a radius of about 5 mm and an arc length of about 5 mm, the second curve has a radius of about 10 mm and an arc length of about 21 mm, and the third curve has a radius of about 4 mm and arc length of about 9 mm.

7. The apparatus of claim 5 wherein the first, second, and third curves are co-planar, and further wherein the first curve has a radius of about 5 mm and an arc length of about 5 mm, the second curve has a radius of about 10 mm and an arc length of about 21 mm, and the third curve has a radius of about 4 mm and arc length of about 15 mm.

8. The apparatus of claim 1 wherein the apparatus has an overall width dimension, w, of from about 4 to about 14 mm.

9. The apparatus of claim 8 wherein the apparatus has an overall width dimension, w, of from about 7 to about 11 mm.

10. The apparatus of claim 9 wherein the apparatus has an overall width dimension, w, of about 9 mm.

11. The apparatus of claim 1, wherein the lead first curve and the lead second curve are helical.

12. The apparatus of claim 1, wherein the lead first curve and the lead second curve are co-planar.

13. The apparatus of claim 1, wherein the lead first curve and the lead second curve are non-planar.

14. A left-ventricular cardiac pacing device comprising:
   a lead having an elongated, flexible body including a lumen extending along its length, the lead having a proximal portion and a distal portion and a lead first curve and a lead second curve having opposing curvatures; and
   a torquing means for effecting rotation of the distal portion of the lead;
   wherein the torquing means comprises a stylet receivable in the lumen, the stylet having a stylet proximal portion and a stylet distal portion, the stylet distal portion including a first curve and a second curve substantially similar to the lead curves, wherein when the stylet is positioned in the lumen, the stylet forms corresponding curves in the distal portion of the lead, such that a torque applied to the stylet proximal portion is transferred to the distal portion of the lead.

15. The device of claim 14 wherein an assembly of the lead and the stylet has an overall width dimension, w, of from about 4 to about 14 mm.

16. The device of claim 15 wherein the assembly has an overall width dimension, w, of from about 7 to about 11 mm.

17. The device of claim 16 wherein the assembly has an overall width dimension, w, of about 9 mm.

18. A method of advancing a lead into a patient's coronary venous system, the method comprising:
   embedding a distal tip of a guiding catheter in the patient's coronary sinus ostium;
   providing a lead having an elongated, flexible body including a lumen extending along its length, the lead having a proximal portion and a distal portion;
   further providing a stylet receivable in the lumen and extending substantially from the proximal to the distal portions of the lead, the stylet having a stylet proximal portion and a stylet distal portion, the stylet distal portion including a first curve and a second curve having opposing curvatures, wherein when the stylet is positioned in the lumen, forming a lead assembly, the stylet forms corresponding curves in the lead distal portion, such that a torque applied to the stylet proximal portion is transferred to the distal portion of the lead;
   advancing the lead assembly through the guiding catheter into the patient's coronary sinus; and
   torquing the stylet to cause rotation of the lead to select a coronary branch vessel.

19. The method of claim 18 wherein providing includes providing a lead further including a lead first curve and a lead second curve substantially similar to the curves of the stylet.

20. The method of claim 18 further comprising determining an angular orientation of the lead distal portion and determining whether a tip of the lead assembly is directed toward or away from a coronary branch vessel.

21. The method of claim 20 further comprising advancing the lead assembly into a branch vessel of the coronary sinus and seating the tip of the lead in the branch vessel.

22. The method of claim 21 further comprising withdrawing the stylet from the assembly, and withdrawing the guiding catheter from the venous system.

* * * * *

UNITED STATES PATENT AND TRADEMARK OFFICE
CERTIFICATE OF CORRECTION

PATENT NO. : 7,280,876 B1
APPLICATION NO. : 10/992359
DATED : October 9, 2007
INVENTOR(S) : Bruce A. Tockman et al.

It is certified that error appears in the above-identified patent and that said Letters Patent is hereby corrected as shown below:

Title Page
Item [75], Inventors, delete the name "Hauge" and replace it with -- Hague --

Signed and Sealed this

Eighteenth Day of March, 2008

JON W. DUDAS
*Director of the United States Patent and Trademark Office*